United States Patent
Meyer et al.

(10) Patent No.: US 9,974,721 B2
(45) Date of Patent: May 22, 2018

(54) COSMETIC COMPOSITION FOR LIGHTENING SKIN AND HAIR

(71) Applicant: Symrise AG, Holzminden (DE)

(72) Inventors: Imke Meyer, Bodenwerder (DE); Mirjam Knupfer, Holzminden (DE); Holger Joppe, Dassel (DE); Antje Köhler, Holzminden (DE); Bernd Hölscher, Halle (DE); Marc Mansfeld, Brevörde (DE)

(73) Assignee: Symrise AG, Holzminden (DE)

( * ) Notice: Subject to any disclaimer, the term of this patent is extended or adjusted under 35 U.S.C. 154(b) by 0 days. days.

(21) Appl. No.: 15/021,489

(22) PCT Filed: Sep. 26, 2014

(86) PCT No.: PCT/EP2014/070701
§ 371 (c)(1),
(2) Date: Mar. 11, 2016

(87) PCT Pub. No.: WO2015/044390
PCT Pub. Date: Apr. 2, 2015

(65) Prior Publication Data
US 2017/0112736 A1    Apr. 27, 2017

(30) Foreign Application Priority Data
Sep. 26, 2013 (EP) ..................... 13186143

(51) Int. Cl.
| | |
|---|---|
| *A61Q 19/02* | (2006.01) |
| *A61K 8/97* | (2017.01) |
| *A61K 8/34* | (2006.01) |
| *A61Q 5/00* | (2006.01) |
| *A61Q 5/02* | (2006.01) |
| *A61Q 5/08* | (2006.01) |
| *A61Q 11/00* | (2006.01) |
| *A61Q 15/00* | (2006.01) |
| *A61Q 17/04* | (2006.01) |
| *A61Q 19/00* | (2006.01) |
| *A61Q 19/08* | (2006.01) |
| *A61Q 5/06* | (2006.01) |
| *A61Q 19/10* | (2006.01) |

(52) U.S. Cl.
CPC ............... *A61K 8/345* (2013.01); *A61Q 5/00* (2013.01); *A61Q 5/02* (2013.01); *A61Q 5/08* (2013.01); *A61Q 11/00* (2013.01); *A61Q 15/00* (2013.01); *A61Q 17/04* (2013.01); *A61Q 19/00* (2013.01); *A61Q 19/02* (2013.01); *A61Q 19/08* (2013.01); *A61K 2800/92* (2013.01); *A61Q 5/06* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 3,427,328 A | 2/1969 | Sandermann et al. | |
| 2008/0069784 A1 | 3/2008 | Millikin | |
| 2011/0038968 A1* | 2/2011 | Rana | A61K 8/602 424/770 |
| 2012/0045407 A1* | 2/2012 | Kaur | A61K 8/0208 424/62 |
| 2013/0295036 A1* | 11/2013 | Philippov | A61Q 19/00 424/74 |
| 2014/0309300 A1* | 10/2014 | Schaefer | A61K 31/047 514/510 |

FOREIGN PATENT DOCUMENTS

WO   2010/097480 A2   9/2010

OTHER PUBLICATIONS

SpecialChem, an electronic article from https://cosmetics.specialchem.com/ [retrieved on May 18, 2009]. Retrieved from the Internet: <URL: https://cosmetics.specialchem.com/news/product-news/highly-effective-skin-lightener>. (Year: 2009).*

* cited by examiner

*Primary Examiner* — Robert T. Crow
*Assistant Examiner* — John P Nguyen
(74) *Attorney, Agent, or Firm* — Dilworth & Barrese, LLP

(57) ABSTRACT

Suggested is a composition comprising (a) larixol and at least one of the components (b1) to (b5) selected from (b1) tyrosinase inhibitors; (b2) sun protection factors; (b3) antioxidants; (b4) anti-inflammatory agents; and (b5) desquamating agents.

15 Claims, No Drawings

COSMETIC COMPOSITION FOR LIGHTENING SKIN AND HAIR

FIELD OF INVENTION

The present invention relates to the area of cosmetics and refers to the use of cosmetic formulations comprising larixol and preferably the use of larixol as a potent agent in cosmetic compositions for lightening skin and hair.

STATE OF THE ART

Skin-lightening active ingredients intervene in one form or another in melanin metabolism or catabolism. Melanin pigments, which are normally brown to black in colour, are formed in the melanocytes of the skin, transferred to the keratinocytes and give the skin or hair its colour. In mammals, the brown-black eumelanins are primarily formed from hydroxy-substituted aromatic amino acids such as L-tyrosine and L-DOPA, the yellow to red pheomelanins additionally from sulfur-containing molecules. Starting from L-tyrosine, L-3,4-dihydroxyphenylalanine (L-DOPA) is formed by the copper-containing key enzyme tyrosinase and is in turn converted by tyrosinase to dopachrome. By a series of steps catalysed by various enzymes, the latter is oxidised to form melanin.

Skin-lightening agents are used for various reasons: if for some reason the melanin-forming melanocytes in human skin are not evenly distributed, pigment spots occur which are either lighter or darker than the surrounding skin area. To overcome this problem, skin and hair lightening agents are sold which at least partially help to balance out such pigment spots. In addition, many people have a need to lighten their naturally dark skin colour or to prevent skin pigmentation. This requires very safe and effective skin and hair lightening agents. Many skin and hair lightening agents contain more or less powerful tyrosinase inhibitors. This is only one possible route towards skin and hair lightening, however.

The melanin production is often stimulated as a result of an inflammation, a process called postinflammatory hyperpigmentation. A hair removal by shaving and/or depilation can induce postinflammatory hyperpigmentation. An example, but not limited to, is the hair removal in the arm pits. Skin insults that result in inflammation/irritation can induce postinflammatory hyperpigmentation. Among such insults are acne lesions, ingrown hairs, scratches, insect bites, and surfactant damage. One of the most common forms of postinflammatory hyperpigmentations is tanning following exposure to sunlight as a response to UV damage to skin. Although in the latter, there may not be visible erythema, histologically, such exposed skin has elevated inflammatory/irritant cell content, yielding a "subclinical" inflammatory/irritant process. Thus to prevent inflammation/irritation of the skin is beneficial regarding the inhibition of melanogenesis in the skin.

Furthermore, UV-absorbing substances are also used to protect against the increase in skin pigmentation caused by UV light. This is a purely physically induced effect, however, and must be distinguished from the biological action of skin-lightening agents on cellular melanin formation, which can also be detected in the absence of UV light. Moreover, UV absorbers do not bring about a true lightening of the skin but merely inhibit the increase in skin pigmentation caused by UV light.

Cosmetic or pharmaceutical (therapeutic) preparations with skin and/or hair lightening activity are known from the prior art. For example, U.S. Pat. No. 4,959,393 (Kuraray) discloses 4-alkyl-resorcinols as skin and/or hair lightening agents.

WO 2004 105736 A1 (Symrise) teaches certain diphenyl-methane-derivatives as skin and/or hair lightening agents.

WO 2007 110415 A1 (Symrise) proposes certain diacetyl trimers as skin and/or hair lightening agents.

WO 2010 122178 A1 and WO 2010 097480 A1 (Symrise) disclose cyclohexyl carbamates and menthyl carbamates, respectively, as skin and/or hair lightening actives.

U.S. Pat. No. 3,427,328 discloses a process for obtaining fragrances opf the amber-type starting from larixol, which is obtained from terpentine oil . . . .

Hydroquinone, hydroquinone derivatives such as e.g. arbutin, vitamin C, derivatives of ascorbic acid such as e.g. ascorbyl palmitate, kojic acid and derivatives of kojic acid such as e.g. kojic acid dipalmitate, are used in particular in commercial cosmetic or therapeutic skin and hair lightening preparations.

One of the most commonly used skin and hair lighteners is hydroquinone. However, this compound has a cytotoxic effect on melanocytes and is irritating to the skin. For that reason such preparations are no longer authorised for cosmetic applications in Europe, Japan and South Africa, for example. In addition, hydroquinone is very sensitive to oxidation and can be stabilised only with difficulty in cosmetic formulations.

Arbutin (beta-arbutin) is a hydroquinone glucoside, which hydrolyses in situ to form hydroquinone and is therefore just as questionable in toxicological terms as hydroquinone.

Vitamin C and ascorbic acid derivatives have only an inadequate effect on the skin. Furthermore, they do not act directly as tyrosinase inhibitors but instead reduce the coloured intermediate stages of melanin biosynthesis.

Kojic acid (5-hydroxy-2-hydroxymethyl-4-pyranone) is a tyrosinase inhibitor which inhibits its catalytic action by chelating the copper atoms in the enzyme; it is used in commercial skin and hair lightening agents but has a high sensitising potential and causes contact allergies.

The object of the present invention was to remedy the disadvantages of the prior art and in particular to provide effective skin and/or hair lightening actives, in particular skin lightening actives, which preferably achieve skin and/or hair lightening activity which preferably is not based on tyrosinase inhibition.

DESCRIPTION OF THE INVENTION

Object of the present invention is a cosmetic composition comprising larixol. Preferably, said cosmetic composition exhibits enhanced skin and hair lightening efficacy and comprises (a) larixol and at least one of the components (b1) to (b5) selected from
(b1) tyrosinase inhibitors;
(b2) sun protection factors;
(b3) antioxidants;
(b4) anti-inflammatory agents; and
(b5) desquamating agents.

Surprisingly, it has been observed that larixol shows a strong inhibitory activity towards melanin formation in melanocytes. More particularly, larixol shows a pronounced skin and hair melanogenesis inhibiting activity and a skin lightening action. The active does not follow the well-known mechanism of tyrosinase inhibition. The invention therefore particularly relates to cosmetic preparations containing a corresponding effective quantity of larixol, in particular for the topical treatment of pigmentation disorders such as hyperpigmentations (e.g. scar hyperpigmentations, posttraumatic drug-induced hyperpigmentations, post-inflammatory hyperpigmentations i.e. induced by phototoxic reactions or by depilation or by shaving, age-induced hyperpigmentations (e.g. lentigines seniles), ephelides) and for the topical lightening of the skin.

The analogues compound manool was already described as skin lightening active (JP 2006 137705 (Pola) and JP 06072855 (Pola)). But in own experiments we could show that due to the high partition coefficient of manool (calculated value of 7.1) it is difficult to incorporate manool into commonly used cosmetic formulations and if successful with preparing a formulation with manool we observed crystallisation of manool after a few days.

The in own experiments identified larixol has a calculated partition coefficient of 6.0 and can easily be incorporated in different commonly used cosmetic formulations in effective amounts.

Larixol

Larixol (CAS Number 1438-66-0)

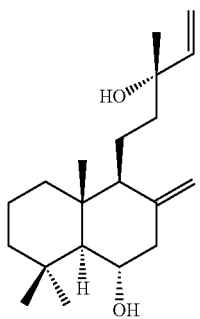

Formula (I)

is a terpenoid compound obtainable for example by saponification of larixyl acetate according to SU 998458. The preferred isomer (+)-larixol is shown in the formula (I) above. This document describes as a source for larixyl acetate larch resin of the so called Amur larch, *Larix amurensis* (also known as *L. gmelinii* or *L. dahurica*).

According to Mills et al. (Phytochemistry 1973, Volume 12, Issue 10, 2407-2412) larixol and larixyl acetate are characteristic for larch resin as they have only been detected in European larch (*L. decidua*) and Duharian larch (*L. gmelinii*) and as they have not been observed in any other genus. In own experiments the larch resin from both aforementioned larch species are appropriate to prepare larixol.

By drilling holes into the trunk of larch trees larch resin can be obtained. Larixyl acetate is the major component of larch resin, whereas larixol is only a minor component.

According to Pferschy-Wenzig et al. (J. Agric. Food Chem. 2008, 56, 11688-11693) larixol and larixyl acetate are also present in larch (*L. decidua*) sawdust and thus in wood. In own experiments we could show that the content of larixyl acetate is significantly higher in resin compared to wood. The harvest of resin is with view to sustainability also preferred compared to the harvest of wood. Thus, for the preparation of larixol the larch resin is used.

Larixol was identified by Marongiu et al. (Journal of Essential Oil Research, 2004, 16:3, 256-261) as a component of the leaves of *Juniperus phoenicea*.

Synonyms for larixol are (1S,4S,4aR)-4-[(3S)-3-hydroxy-3-methyl-pent-4-enyl]-4a,8,8-trimethyl-3-methylene-decalin-1-ol; (+)-(1S,4S,4aR,8aS)-4-((3S)-3-hydroxy-3-methyl-4-pentenyl)-4a,8,8-trimethyl-3-methylenedecahydro-1-naphthalenol; (1S,4S,4aR,8aS)-4-[(3S)-3-Hydroxy-3-methylpent-4-enyl]-4a,8,8-trimethyl-3-methylenedecahydronaphthalen-1-ol; (+)-larixol.

Larixol is an important starting material for fragrant materials as described in detail in US 2006 0224019 (Symrise) and US 2006 0154347 (IFF).

US 2010 0137194 discloses plasminogen activator inhibitor-1 (PAI-1) inhibitors and methods of use of these inhibitors to modulate lipid metabolism. Larixol was identified in the screening as PAI-1 inhibitor. Administration of a therapeutic composition comprising a PAI-1 inhibitor is described in general as an injection. But alternatively also an oral consumption is possible. Topical treatment is not given in the patent.

WO 2013 021038 A1 describes bicyclic labdane diterpenes for use in the treatment of transient receptor potential cation channel-6 (TRPC6) activation associated diseases like pulmonary or renal diseases. Inter alia larixol, larixyl acetate and larixyl diacetate were identified as TRPC6 antagonists. Administration of the identified compounds is oral, inhalational or parenteral, preferred administration is intravenous. A topical treatment is not described in the document.

The amount of larixol for the modulation of skin and hair pigmentation according to the invention is preferably about 0.00001 to about 30% b.w. preferably about 0.0001 to about 20% b.w., particularly preferably about 0.001 to about 5% b.w. based on the total weight of the preparation.

Skin Lightening Agents

Larixol can be accompanied by a second skin and/or hair lightening agent that is preferably a tyrosinase inhibitor (component b1). The amount of tyrosinase inhibitors is preferably about 0.00001 to about 30% b.w. preferably about 0.0001 to about 20% b.w., particularly preferably about 0.001 to about 5% b.w. based on the total weight of the preparation.

Suitable examples encompass kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, *papaya* extract, turmeric extract, mulberry extract, bengkoang extract, nutgrass extract, liquorice root extract or constituents concentrated or isolated therefrom, preferably glabridin or licochalcone A, artocarpus extract, extract of *rumex* and *ramulus* species, extracts of pine species (*pinus*), extracts of *vitis* species or stilbene derivatives isolated or concentrated therefrom, saxifrage extract, scutelleria extract, grape extract and/or microalgae extract, in particular *Tetraselmis suecica* Extract.

Preferred tyrosinase inhibitors as component (b1) are kojic acid and phenylethyl resorcinol, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract (containing glycyrrhizin), alpha-hydroxy-acids, 4-alkylresorcinols, 4-hydroxyanisole.

Particularly preferred are mixtures of larixol and phenylethyl resorcinol (SymWhite 377®) which showed the strongest synergistic inhibitory activity towards melanin formation in melanocytes, when used in a ratio by weight of about 20:80 to about 80:20, and preferably about 40:60 to about 60:40.

These skin lighteners are preferred due to their very good activity, in particular in combination with larixol according to the present invention. In addition, said preferred skin lighteners are readily available.

Sun Protection Factors

The cosmetic compositions according to the present invention may also encompass one of more primary or secondary sun protection factor (component b2) in amounts of about 0.1 to about 30% b.w. preferably about 0.5 to about 15% b.w., particularly preferably about 1 to about 8% b.w. based on the total weight of the preparation.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
p-aminobenzoic acid
p-aminobenzoic acid ethyl ester (25 mol) ethoxylated (INCI name: PEG-25 PABA)
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-phenylbenzimidazole sulfonic acid and salts (Neo Heliopan®Hydro)
3-(4'-trimethylammonium) benzylidene bornan-2-one methyl sulfate
beta-imidazole-4(5)-acrylic acid (urocanic acid)
3-(4'-sulfo)benzylidene bornan-2-one and salts
3-(4'-methyl benzylidene)-D,L-camphor (Neo Heliopan®MBC)
3-benzylidene-D,L-camphor
N-[(2 and 4)-[2-(oxoborn-3-ylidene) methyl]benzyl] acrylamide polymer
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb®HEB)
benzylidene malonate polysiloxane (Parsol®SLX)
glyceryl ethylhexanoate dimethoxycinnamate
dipropylene glycol salicylate
tris(2-ethylhexyl)-4,4',4''-(1,3,5-triazine-2,4,6-triyltriimino) tribenzoate (=2,4,6-trianilino-(p-carbo-2'-ethylhexyl-1'-oxy)-1,3,5-triazine) (Uvinul®T150)

Broadband filters which are preferably combined with one or more compounds of formula (I) in a preparation according to the present invention are selected from the group consisting of
2-ethylhexyl-2-cyano-3,3-diphenyl acrylate (Neo Heliopan®303)
ethyl-2-cyano-3,3'-diphenyl acrylate
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
sodium hydroxymethoxybenzophenone sulfonate
disodium-2,2'-dihydroxy-4,4'-dimethoxy-5,5'-disulfobenzophenone phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl®XL)

2,2'-methylene bis-(6-(2H-benzotriazol-2-yl)-4-1,1,3,3-tetramethylbutyl) phenol) (Tinosorb®M)

2,4-bis-[4-(2-ethylhexyloxy)-2-hydroxyphenyl]-1,3,5-triazine 2,4-bis-[{(4-(2-ethylhexyloxy)-2-hydroxy}phenyl]-6-(4-methoxyphenyl)-1,3,5-triazine (Tinosorb®S)

2,4-bis-[{(4-(3-sulfonato)-2-hydroxypropyloxy)-2-hydroxy}phenyl]-6-(4-methoxyphenyl)-1,3,5-triazine sodium salt 2,4-bis-[{(3-(2-propyloxy)-2-hydroxypropyloxy)-2-hydroxy}phenyl]-6-(4-methoxyphenyl)-1,3,5-triazine 2,4-bis-[{4-(2-ethylhexyloxy)-2-hydroxy}phenyl]-6-[4-(2-methoxyethyl carbonyl) phenylamino]-1,3,5-triazine 2,4-bis-[{4-(3-(2-propyloxy)-2-hydroxypropyloxy)-2-hydroxy}phenyl]-6-[4-(2-ethylcarboxyl) phenylamino]-1,3,5-triazine 2,4-bis-[{4-(2-ethylhexyloxy)-2-hydroxy}phenyl]-6-(1-methylpyrrol-2-yl)-1,3,5-triazine 2,4-bis-[{4-tris-(trimethylsiloxysilylpropyloxy)-2-hydroxy}phenyl]-6-(4-methoxyphenyl)-1,3,5-triazine 2,4-bis-[{4-(2"-methylpropenyloxy)-2-hydroxy}phenyl]-6-(4-methoxyphenyl)-1,3,5-triazine 2,4-bis-[{4-(1',1',1',3',5',5',5'-heptamethylsiloxy-2"-methylpropyloxy)-2-hydroxy}phenyl]-6-(4-methoxyphenyl)-1,3,5-triazine UV-A filters which are preferably combined with one or more compounds of formula (I) in a preparation according to the present invention are selected from the group consisting of 4-isopropyl dibenzoyl methane terephthalylidene dibornane sulfonic acid and salts (Mexoryl®SX)

4-t-butyl-4'-methoxydibenzoyl methane (avobenzone)/(Neo Heliopan®357)

phenylene bis-benzimidazyl tetrasulfonic acid disodium salt (Neo Heliopan®AP)

2,2'-(1,4-phenylene)-bis-(1H-benzimidazole-4,6-disulfonic acid), monosodium salt 2-(4-diethylamino-2-hydroxybenzoyl) benzoic acid hexyl ester (Uvinul® A Plus)

indanylidene compounds in accordance with DE 100 55 940 A1 (=WO 2002 038537 A1)

UV filters which are more preferably combined with one or more compounds of formula (I) in a preparation according to the present invention are selected from the group consisting of p-aminobenzoic acid 3-(4'-trimethylammonium) benzylidene bornan-2-one methyl sulfate salicylic acid homomenthyl ester (Neo Heliopan®HMS)

2-hydroxy-4-methoxybenzophenone (Neo Heliopan®BB)

2-phenylbenzimidazole sulfonic acid (Neo Heliopan®Hydro)

terephthalylidene dibornane sulfonic acid and salts (Mexoryl®SX)

4-tert-butyl-4'-methoxydibenzoyl methane (Neo Heliopan®357)

3-(4'-sulfo)benzylidene bornan-2-one and salts 2-ethylhexyl-2-cyano-3,3-diphenyl acrylate (Neo Heliopan®303)

N-[(2 and 4)-[2-(oxoborn-3-ylidene) methyl]benzyl] acrylamide polymer p-methoxycinnamic acid-2-ethylhexyl ester (Neo Heliopan®AV)

p-aminobenzoic acid ethyl ester (25 mol) ethoxylated (INCI name: PEG-25 PABA)

p-methoxycinnamic acid isoamyl ester (Neo Heliopan®E1000)

2,4,6-trianilino-(p-carbo-2'-ethylhexyl-1'-oxy)-1,3,5-triazine (Uvinul®T150)

phenol, 2-(2H-benzotriazol-2-yl)-4-methyl-6-(2-methyl-3 (1,3,3,3-tetramethyl-1-(trimethylsilyl)oxy)disiloxyanyl) propyl) (Mexoryl®XL)

4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)

3-(4'-methyl benzylidene)-D,L-camphor (Neo Heliopan®MBC)

3-benzylidene camphor salicylic acid-2-ethylhexyl ester (Neo Heliopan®OS)

4-dimethylaminobenzoic acid-2-ethylhexyl ester (Padimate O)

hydroxy-4-methoxybenzophenone-5-sulfonic acid and Na salt 2,2'-methylene bis-(6-(2H-benzotriazol-2-yl)-4-1,1,3,3-tetramethylbutyl) phenol) (Tinosorb®M)

phenylene bis-benzimidazyl tetrasulfonic acid disodium salt (Neo Heliopan®AP)

2,4-bis-[{(4-(2-ethylhexyloxy)-2-hydroxy}phenyl]-6-(4-methoxyphenyl)-1,3,5-triazine (Tinosorb®S)

benzylidene malonate polysiloxane (Parsol®SLX)

menthyl anthranilate (Neo Heliopan®MA)

2-(4-diethylamino-2-hydroxybenzoyl) benzoic acid hexyl ester (Uvinul® A Plus)

indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Antioxidants

The cosmetic compositions according to the present invention may also encompass one of more antioxidant (component b3) in amounts of about 0.1 to about 30% b.w. preferably about 0.5 to about 15% b.w., particularly preferably about 1 to about 10% b.w. based on the total weight of the preparation.

Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonylthreonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, *sophora*, pueraria, *pinus*, citrus, *Phyllanthus emblica* or St. John's wort, grape seeds, wheat germ, *Phyllanthus emblica*, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Anti-Inflammatory Agents

The compositions may also contain anti-inflammatory and/or redness and/or itch ameliorating ingredients (component b4) in amounts of about 0.1 to about 30% b.w.

preferably about 0.5 to about 15% b.w., particularly preferably about 1 to about 10% b.w. based on the total weight of the preparation.

Preferred are steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, *Commiphora* species, *Rubia* species, willow, willow-herb, oats, *calendula, arnica*, St John's wort, honeysuckle, rosemary, *Passiflora incarnata*, witch hazel, ginger or *Echinacea*; preferably selected from the group consisting of extracts or fractions from camomile, Aloe vera, oats, *calendula, arnica*, honeysuckle, rosemary, witch hazel, ginger or *Echinacea*, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

Desquamating Agents

The compositions may also contain desquamating agents (component b5) in amounts of about 0.1 to about 30% b.w. preferably about 0.5 to about 15% b.w., particularly preferably about 1 to about 10% b.w. based on the total weight of the preparation.

The expression "desquamating agent" is understood to mean any compound capable of acting:
either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of *Sophora japonica*; resveratrol and some derivatives of jasmonic acid;
or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

INDUSTRIAL APPLICATION

In accordance with the present invention the composition can be a cosmetic composition, a pharmaceutical composition or a dietary supplement composition. Preferred fields of use of larixol according to the invention are dermatological formulations or products which serve for treatment, care and/or cleansing of the skin and/or hair or as a make-up product in decorative cosmetics, in particular as products for dermatological light protection.

Cosmetic and/or Pharmaceutical Compositions

The preparations according to the invention may contain abrasives, anti-acne agents, agents against ageing of the skin, anti-cellulitis agents, antidandruff agents, astringents, perspiration-inhibiting agents, antiseptic agents, anti-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, strengthening agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-protecting agents, skin-softening agents, hair promotion agents, cooling agents, skin-cooling agents, warming agents, skin-warming agents, stabilizers, suspending agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, pigments, aromas, flavouring substances, odoriferous substances, polyols, surfactants, electrolytes, organic solvents or silicone derivatives and the like as additional auxiliaries and additives.

Surfactants

Other preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:
  products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
  $C_{12/18}$ fatty acid monoesters and diesters of addition products of 1 to 30 mol ethylene oxide onto glycerol;
  glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan Esters.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol Esters.

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic Emulsifiers.

Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric Emulsifiers.

Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grinau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlising Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Anti-Ageing Actives

In the context of the invention, anti-ageing or biogenic agents are, for example antioxidants, matrix-metalloproteinase inhibitors (MMPI), skin moisturizing agents, glycosaminglycan stimulkators, anti-inflammatory agents, TRPV1 antagonists and plant extracts.

Matrix-Metalloproteinase Inhibitors (MMPI).

Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1 (2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, *Oenothera biennis* root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, *Rubus Fruticosus* (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-Moisturizing Agents.

Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan Stimulators.

Preferred compositions comprise substances stimulating the synthesis of glycosaminoglycans selected from the group consisting of hyaluronic acid and derivatives or salts, Subliskin (Sederma, INCI: *Sinorhizobium Meliloti* Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, *Sinorhizobium Meliloti* Ferment Filtrate, Calcium ketogluconate, *Alpinia galanga* leaf extract and tetradecyl aminobutyroylvalylaminobutyric urea trifluoroacetate.

TRPV1 Antagonists.

Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

Anti-Cellulite Agents.

Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, ananas extract and conjugated linoleic acid.

Fat Enhancing Agents.

Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxacum*), *Orthosiphon*, *Vitex*, *Coffea*, *Paullinia*, *Theobroma*, *Asiasarum*, *Cucurbita* or *Styphnolobium*, *Serenoa repens* (saw palmetto), *Sophora flavescens*, *Pygeum africanum*, *Panicum miliaceum*, *Cimicifuga racemosa*, *Glycine max*, *Eugenia caryophyllata*, *Cotinus coggygria*, *Hibiscus rosa-sinensis*, *Camellia sinensis*, *Ilex paraguariensis*, *Isochrysis galbana*, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gammaglutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus*, *Gloiopeltis*, *Ceramium*, *Durvillea*, *Glycine max*, *Sanguisorba officinalis*, *Calendula officinalis*, *Hamamelis virginiana*, *Arnica montana*, *Salix alba*, *Hypericum perforatum* or *Gymnema sylvestre*.

Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (l-menthoxy)-1,2-propandiol, (l-menthoxy)-2-methyl-1,2-propandiol, l-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, monomenthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (l-(–)-isopulegol, l-(–)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odourneutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for exampie, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

Dietary Supplements

In as far the compositions according to the present invention represent dietary supplements, they are administered orally, preferably as a spray dried composition or a capsule.

The compositions are typically encapsulated by means of a solid covering material, which is preferably selected from starches, degraded or chemically or physically modified starches (in particular dextrins and maltodextrins), gelatins, gum arabic, agar-agar, ghatti gum, gellan gum, modified and non-modified celluloses, pullulan, curdlan, carrageenans, alginic acid, alginates, pectin, inulin, xanthan gum and mixtures of two or more of said substances.

The solid covering material is preferably selected from gelatin (preferred are pork, beef, chicken and/or fish gelatins and mixtures thereof, preferably comprising at least one gelatin with a bloom value of greater than or equal to 200, preferably with a bloom value of greater than or equal to 240), maltodextrin (preferably obtained from maize (corn), wheat, tapioca or potato, preferred maltodextrins have a DE value of 10-20), modified cellulose (for example cellulose ether), alginates (for example Na-alginate), carrageenan (beta-, iota-, lambda- and/or kappa carrageenan), gum arabic, curdlan and/or agar-agar. Gelatin is preferably used, in particular, because of its good availability in different bloom values. Particularly preferred, especially for oral use are seamless gelatin or alginate capsules, the covering of which dissolves very rapidly in the mouth or bursts when chewing. Production may take place, for example, as described in EP 0389700 A1, U.S. Pat. No. 4,251,195, U.S. Pat. No. 6,214,376, WO 2003 055587 or WO 2004 050069 A1.

The capsules, however, may also represent micro-capsules. "Microcapsules" are understood to be spherical aggregates with a diameter of about 0.1 to about 5 mm which contain at least one solid or liquid core surrounded by at least one continuous membrane. More precisely, they are finely dispersed liquid or solid phases coated with film-forming polymers, in the production of which the polymers are deposited onto the material to be encapsulated after emulsification and coacervation or interfacial polymerization. In another process, liquid active principles are absorbed in a matrix ("microsponge") and, as microparticles, may be additionally coated with film-forming polymers. The microscopically small capsules, also known as nanocapsules, can be dried in the same way as powders. Besides single-core microcapsules, there are also multiple-core aggregates, also known as microspheres, which contain two or more cores distributed in the continuous membrane material. In addition, single-core or multiple-core microcapsules may be surrounded by an additional second, third etc. membrane. The membrane may consist of natural, semisynthetic or synthetic materials. Natural membrane materials are, for example, gum arabic, agar agar, agarose, maltodextrins, alginic acid and salts thereof, for example sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic membrane materials are inter alia chemically modified celluloses, more particularly cellulose esters and ethers, for example cellulose acetate, ethyl cellulose, hydroxypropyl cellulose, hydroxypropyl methyl cellulose and carboxymethyl cellulose, and starch derivatives, more particularly starch ethers and esters. Synthetic membrane materials are, for example, polymers, such as polyacrylates, polyamides, polyvinyl alcohol or polyvinyl pyrrolidone.

Examples of known microcapsules are the following commercial products (the membrane material is shown in brackets) Hallcrest Microcapsules (gelatin, gum arabic), Coletica® Thalaspheres (maritime collagen), Lipotec® Millicapseln (alginic acid, agar agar), Induchem® Unisheres® (lactose, microcrystalline cellulose, hydroxypropyimethyl cellulose), Unicetin C30 (lactose, microcrystalline cellulose, hydroxypropylmethyi cellulose), Kobe Glycospheres, (modified starch, fatty acid esters, phospholipids), Softspheres™ (modified agar agar) and Kuhs Probiol Nanospheres (phospholipids).

Medicaments

The invention also encompasses a medicament comprising larixol for inhibiting melanin formation in melanocytes.

Methods and Uses

Another object of the present invention is a non-therapeutical method for lightening skin and hair by applying a working amount of larixol to a human, for example by means of a cream, a lotion, a gel, or a spray. Preferably, the active composition is applied topically to the mammal or the keratin fibres, but it is also possible to administer the compositions orally, for example by means of a capsule, a candy or a chewing-gum.

Finally, the invention also encompasses the use of larixol as a cosmetic agent for lightening skin and hair.

It should be understood, that the methods and uses claimed above encompass the same preferred elements and inventive embodiments as explained above in more detail.

EXAMPLES

Example 1

Depigmentation Effect on Melanoma Cell Cultures

B16V mouse melanoma cells are disseminated in a 96-well micro-titre plate in a concentration of $7.5 \times 10^3$ cells/well. After cultivation for 24 h at 37° C. and 5% $CO_2$ in RPMI medium, enriched with 10% foetal calf serum, various concentrations of the test substances and 0.3 mM tyrosine and 10 nM α-MSH (α-melanocyte stimulating hormone) are added and incubated for a further 96 h. The maximum concentration of the test substances used corresponds to 0.1 times the value of the $IC_{20}$ value of the cytotoxicity assay. Only tyrosine and α-MSH are added to the controls. After incubation, sodium hydroxide solution (final concentrations: 1 M) is added to the culture medium and the absorption (A) is measured after 3 h at 400 nm.

The inhibition of pigmentation in the presence of the test compounds was calculated using the following equation:

Inhibition of pigmentation (%)=100−[($A_{test\ compound}$/$A_{control}$)×100]

wherein $A_{test\ compound}$=absorption of the wells with test substance and with cells $A_{control}$=absorption of the wells without test substance, but with cells From the inhibition of pigmentation (%) in a series of dilutions of test compounds, the $IC_{50}$ for each test compound is calculated. This is the concentration of a test compound at which pigmentation is inhibited by 50%. The results are compiled in Table 1:

TABLE 1

| Inhibition of pigmentation | |
| --- | --- |
| Test substance | $IC_{50}$ [μM] |
| Kojic acid (reference) | 452.3 |
| beta-Arbutin (reference) | 67.0 |
| Larixol | 3.9 |

Example 2

Synergistic In Vitro Melanin Inhibition

Experimental procedure as described in Example 1. The results are compiled in Table 2.

TABLE 2

| Melanin inhibition | | | | | |
| --- | --- | --- | --- | --- | --- |
| Example | Kull variable | Substance | IC50 [%] | Percentage in mixture (Kull variable D/E) | Synergy Index (SI) |
| 1 | A | Larixol | 0.00011% | 75% | 0.71 |
|   | B | SymWhite ® 377 | 0.000034% | 25% |   |
|   | C | Larixol + SymWhite ® 377 | 0.000050% |   |   |
| 2 | A | Larixol | 0.00011% | 75% | 0.91 |
|   | B | SymWhite ® 377 | 0.000021% | 25% |   |
|   | C | Larixol + SymWhite ® 377 | 0.000047% |   |   |

The Synergy Index (SI)[1] is calculated according to Kull's equation as follows:

[1] The calculation of the synergy index (SI-value) was carried out on the basis of following literature: D. C. Steinberg, Cosmetics & Toiletries 2000, 115 (11), 59-62 and F. C. Kull et al., Applied Microbiology 1961, 9, 538-541.

$$SI = \frac{C*D}{A} + \frac{C*E}{B}$$

with

A: individual IC50 of substance A

B: individual IC50 of substance B

C: IC50 of the mixture of A and B

D: percentage of substance A in the mixture

E: percentage of substance B in the mixture

In accordance to the given examples in the literature, in which reduced values for A, B and C (i.e. the minimal concentration of inhibition in antimicrobial tests) mean better activity and consequently SI values <1 document a synergistic effect, decreasing values of the IC50 mean better efficacy. According to Kull's equation the evidence for a synergistic effect results for SI values <1.

In the experiments with Larixol und SymWhite® 377 the calculated SI values obviously are below 1 (experiments 1 and 2). From this it follows that a composition of Larixol and SymWhite® 377 constitutes a potent synergistic combination of active ingredients

Example 3

Depigmentation Effect on Ex Vivo Skin

Human skin, originating from plastic surgery, was cut into 4×4×3 mm pieces (length×width×height) and placed in culture at the air-liquid interface on a sterilized cotton pad soaked with 5 ml of customized DMEM (Dulbecco's Modified Eagle Medium). Assays were started 24 h after sample acclimatization at 37° C., 5% $CO_2$. O/W emulsions (as described in more detail below) without (=control) and with the test compounds, respectively, were applied topically and incubated for 6 days. Histological sections were prepared and melanin granules stained by Fontana-Masson technique. The granules were quantified by image analysis. The results are compiled in Tables 3.1 and 3.2.

TABLE 3.1

Depigmentation effect of larixol on ex vivo skin

| Test substance | Amount in wt. % | Melanin score vs. Control |
|---|---|---|
| Larixol | 0.1% | −41% |

TABLE 3.2

Composition of the O/W emulsions used for the ex vivo study (amounts in % b.w.)

| Phase | Ingredient | INCI-Name | Amount |
|---|---|---|---|
| A | Water | Water (Aqua) | Ad 100 |
|   | Hydrolite-5 | 1,2 Pentylene Glycol | 2.00 |
| B | PCL liquid 100 | Cetearyl Octanoate | 3.00 |
|   | Lanette O | Cetearyl Alcohol | 2.00 |
|   | Paraffin oil 5° E | Mineral Oil | 3.00 |
|   | Eutanol G | Octyldodecanol | 4.00 |
|   | Abil 350 | Dimethicone | 0.50 |
| C | Pemulen TR1 | Acrylates/C10-30 Alkyl Acrylate Crosspolymer | 0.20 |
|   | Ultrez-21 | Acrylates/C10-30 Alkyl Acrylate Crosspolymer | 0.05 |
| D | NaOH, 10% solution | Sodium Hydroxide | 0.50 |
| E | Larixol |  | 0.10 |

Manufacturing Procedure

Phases A and B are heated to 70° C. separately. Pemulen TR1 as well as Ultrez-21 are dispersed in phase B when heated to 70° C. Phase B/C is added to phase A by mixing with an Ultra Turrax, followed by emulsifying. Phase D is slowly added to phase A/B/C using a paddle mixer and a pH 5.5-6 is adjusted. The formulation is cooled down while mixing with a paddle mixer. Phase E is added to the mixture of phase A-D.

Examples 4-14

Skin and Hair Care Products

In the following the present invention is illustrated in more detail by various formulation examples:
4=Skin Care Gel (SPF 6)
5=Sun Protection Lotion SPF 24 (UVA/UVB Balance)
6=Tinted Anti-aging Balm, SPF 15
7=Body Lotion, SPF 15
8=Skin Soothing Night Cream O/W
9=Cream W/O
10=Skin Care Ampoule
11=Skin Oil
12=Shower & Shampoo
13=Tinted Skin Care Stick SPF 50
14=Hair Gel In Formulation Examples 5-15 the following two perfume oils PFO1 and PFO2 were each used as fragrance (DPG=dipropylene glycol).

TABLE A

Perfume oil PFO1 with rose smell (amounts in parts b.w.)

| Component | Amount |
|---|---|
| Acetophenone, 10% in DPG | 10.00 |
| n-Undecanal | 5.00 |
| Aldehyde C14, so-called (peach aldehyde) | 15.00 |
| Allylamyl glycolate, 10% in DPG | 20.00 |
| Amyl salicylate | 25.00 |
| Benzyl acetate | 60.00 |
| Citronellol | 80.00 |
| d-Limonene | 50.00 |
| Decenol trans-9 | 15.00 |
| Dihydromyrcenol | 50.00 |
| Dimethylbenzylcarbinyl acetate | 30.00 |
| Diphenyloxide | 5.00 |
| Eucalyptol | 10.00 |
| Geraniol | 40.00 |
| Nerol | 20.00 |
| *Geranium* oil | 15.00 |
| Hexenol cis-3, 10% in DPG | 5.00 |
| Hexenyl salicylate cis-3 | 20.00 |
| Indole, 10% in DPG | 10.00 |
| Alpha-ionone | 15.00 |
| Beta-ionone | 5.00 |
| Lilial ® (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrolyl acetate | 20.00 |
| Terpineol | 30.00 |
| Tetrahydrolinalool | 50.00 |
| Cinnamyl alcohol | 10.00 |
| Total: | 1,000.00 |

TABLE B

Perfume oil PFO2 with white blossom and musk smell (amounts in parts b.w.)

| Component | Amount |
|---|---|
| Benzyl acetate | 60.00 |
| Citronellyl acetate | 60.00 |
| Cyclamenaldehyde (2-methyl-3-(4-isopropylphenyl)propanal | 20.00 |
| Dipropylene glycol (DPG) | 60.00 |
| Ethyllinalool | 40.00 |
| Florol (2-isobutyl-4-methyltetrahydro-2H-pyran-4-ol) | 30.00 |
| Globanone ® [(E/Z)-8-cyclohexadecen-1-one] | 180.00 |
| Hedione ® (methyldihydrojasmonate) | 140.00 |
| Hexenyl salicylate, cis-3 | 10.00 |
| Vertocitral (2,4-dimethyl-3-cyclohexenecarboxaldehyde) | 5.00 |
| Hydratropaaldehyde, 10% in DPG | 5.00 |
| Isodamascone (1-(2,4,4-trimethyl-2-cyclohexen-1-yl)-2-buten-1-one, 10% in DPG | 5.00 |
| Isomuscone (cyclohexadecanone) | 40.00 |
| Jacinthaflor (2-methyl-4-phenyl-1,3-dioxolane) | 10.00 |
| Cis-jasmone, 10% in DPG | 20.00 |
| Linalool | 50.00 |
| Linalyl acetate | 30.00 |
| Methyl benzoate, 10% in DPG | 25.00 |
| para-Methyl cresol, 10% in DPG | 10.00 |
| Nerol | 20.00 |
| Phenylpropylaldehyde | 5.00 |
| 2-Phenylethyl alcohol | 82.00 |
| Tetrahydrogeraniol | 13.00 |
| 2,2-Dimethyl-3-cyclohexyl-1-propanol | 80.00 |
| Total: | 1,000.00 |

TABLE 5

| | | Skin whitening compositions | | | | | | | | | | |
|---|---|---|---|---|---|---|---|---|---|---|---|---|
| Ingredients | INCI-Name | 4 | 5 | 6 | 7 | 8 | 9 | 10 | 11 | 12 | 13 | 14 |
| | | Skin whitening ingredients | | | | | | | | | | |
| Larixol | | 0.1 | 1 | 0.05 | 0.2 | 1 | 0.5 | 0.02 | 0.5 | 0.2 | 1 | 0.5 |
| SymWhite 377 (Symrise) | Phenylethyl resorcinol | | 0.5 | | | | | 0.1 | | | | |
| beta-Arbutin | Arbutin | | | | | | 0.5 | | | | | |
| Nicotinamide | Niacinamide | | | | | | | | | | 1 | |
| Kojic acid | Kojic acid | | | 0.5 | | | | | | | | 1 |
| Mg ascorbyl phosphate | Magnesium ascorbyl phosphate | | | 5 | | | | | | | 3 | |
| Actipone ® Mulberry GW (Symrise) | Aqua, Glycerin, *Morus Alba* Root Extract | 2 | | | | | | | | | | |
| (3-Methoxy-propyl)-carbamic acid (1R,2S,5R)-2-isopropyl-5-methyl-cyclohexyl ester | | | | | | | | | | | 0.5 | |
| p-Tolyl-carbamic acid 3,5-dimethyl-cyclohexyl ester | | | 1 | | | | | | | | | |
| (2-Methoxy-phenyl)-carbamic acid 3,3,5-trimethyl-cyclohexyl ester | | | | | | | | | | 0.5 | | |
| | | Other Ingredients | | | | | | | | | | |
| (−) alpha Bisabolol nat. | Bisabolol | | | 0.1 | | 0.2 | | | | | 0.1 | |
| Abil 350 | Dimethicone | | | | 2 | | | | | | | |
| Actipone ® *Laminaria Saccharina*GW | Glycerin, Water (Aqua), *Laminaria Saccharina* Extract | | | | | | 1 | | | | | |
| Aloe Vera Gel Conc. 10:1 | Aloe Barbadensis Leaf Juice | | | 1 | | | | | | | | |
| Aluminium Stearate | Aluminium Stearate | | | | | | | | 1.2 | | | |
| Amaze XT | Dehydroxanthan Gum | | 1.4 | | | | | | | | | |
| Betulin 90% (1079) | Betulin | | | | | 0.15 | | | | | | |
| Biotive ® L-Arginine | Arginine | | 3.2 | 0.5 | 0.6 | 0.9 | | | | | | |
| Biotive ® Troxerutin | Troxerutin | | | 0.5 | 0.5 | | | | | | | |
| Carbopol ETD 2020 | Acrylates/C10-30 Alkyl Acrylate Crosspolymer | | 0.2 | | | | | | | | | |
| Carbopol ETD 2050 | Carbomer | | | 0.2 | | | 0.2 | | | | | |
| Carbopol Ultrez-21 | Acrylates/C10-30 Alkyl Acrylate Crosspolymer | | | | | 0.5 | | | | | | |
| Citric Acid 10% sol. in water | Citric Acid | | | | | | | | | 3.1 | | |
| Comperlan 100 | Cocamide MEA | | | | | | | | | 1 | | |
| Corapan TQ | Diethylhexyl 2,6 Naphtalate | | | | | 3 | | | | | | |
| Crinipan ® AD | Climbazole | | | | | | | | | | | 0.1 |
| Cutina GMS V | Glyceryl Stearate | | | | | | 2 | | | | | |
| Cutina PES | Pentaerythrityl Distearate | | | | 2 | | | | | | | |
| Cutina TS | PEG-3 Distearate | | | | | | | | | 2.5 | | |
| DC9701 Cosmetic Powder | Dimethicone/Vinyl Dimethicone Crosspolymer, Silica | | | | | | | | | | 2 | |
| Dermacryl AQF | Acrylates Copolymer | | | 2 | | | | | | | | |
| Dipropylene Glycol | Dipropylene Glycol | | | | | | | | | | | 1 |
| Dow Corning 193 surfactant | PEG-12 Dimethicone | | 1 | | | | | | | | | |
| Dow Corning 246 fluid | Cyclohexa-siloxane | | | 3 | | | 1 | | | | | |

TABLE 5-continued

Skin whitening compositions

| Ingredients | INCI-Name | 4 | 5 | 6 | 7 | 8 | 9 | 10 | 11 | 12 | 13 | 14 |
|---|---|---|---|---|---|---|---|---|---|---|---|---|
| D-Panthenol 75 L | Panthenol | | | | | | | 1 | | 0.3 | | 0.5 |
| Dracorin ® CE | Glyceryl Stearate/Citrate | | | | | 3 | | | | | | |
| Dracorin ® GOC | Glyceryl Oleate Citrate, Caprylic Capric Triglyceride | | | | 1.5 | | | | | | 0.5 | |
| Drago-Beta-Glucan | Water (Aqua), Butylene Glycol, Glycerin, *Avena Sativa* (Oat) Kernel Extract | | | | | 1 | | | | | | |
| DragoCalm ® | Water, Glycerin, *Avena Sativa* (Oat Kernel Extract) | | | | | | | 1 | | | | |
| Dragocide ® Liquid | Phenoxyethanol, Methylparaben, Ethylparaben, Butylparaben, Propylparaben, Isobutylparaben | | | | | 0.8 | | | | | | |
| Dragoderm ® | Glycerin, *Triticum Vulgare* (Wheat) Gluten, Water (Aqua) | | | | | 2 | | | | | | |
| Dragosan W/O P | Sorbitan Isostearate, Hydrogenated Castor Oil, Ceresin, Beeswax (Cera Alba) | | | | | | 8 | | | | | |
| Dragosantol ® 100 | Bisabolol | | | 0.1 | | | 0.2 | | | | | |
| Dragosine ® | Carnosine | 0.2 | | | | | | 0.2 | | | | |
| Dragoxat ® 89 | Ethylhexyl Isononanoate | | 2 | 5 | | 4 | 7 | | 15 | | 5 | |
| EDTA B | Tetrasodium EDTA | | | | | | | 0.1 | | | | |
| EDTA BD | Disodium EDTA | | 0.1 | 0.1 | 0.1 | | | | | | | 0.1 |
| Emulsiphos ® | Potassium Cetyl Phosphate, Hydrogenated Palm Glycerides | | 2 | 2 | | | | | | | | |
| Ethanol | Ethanol | 10 | | | | | | | | | | |
| Extrapone ® *Ginkgo Biloba* | Propylene Glycol, Water (Aqua), *Ginkgo Biloba* Leaf Extract, Glucose, Lactic Acid | | | | | | 1 | | | | | |
| Food Color Brown E172 + E171 Powder | Color | | | | 2 | | | | | | 3 | |
| Fragrance PFO1 or PFO2 | Parfum | 0.1 | 0.2 | 0.3 | 0.2 | 0.4 | 0.3 | 0.1 | 0.5 | 1 | | 0.1 |
| Frescolat ® MGA | Menthone Glycerin Acetal | | | | | | | 0.1 | | | | |
| Frescolat ® ML | Menthyl Lactate | | | | | | | | | | 0.2 | |
| Fruitapone ® Orange B | Propylene Glycol, Water (Aqua), Citric Acid, *Citrus Aurantium Dulcis* (Orange) Juice, Trideceth-9, Bisabolol | | | | | | | | | | | 0.5 |
| Glycerine 99.5% | Glycerin | 2.5 | 3 | | | 5 | 3 | | | 0.5 | | 10 |
| Hydrolite ®-5 | Pentylene Glycol | 3 | 2 | | 5 | | | | | 1 | | |
| Hydroviton ®-24 | Water, Pentylene Glycol, Glycerin, Lactic Acid, Sodium Lactate, Serine, Urea, Sorbitol, Sodium Chloride, Allantoin | | | | | 1 | 1 | | 10 | | | |
| Iso Adipat | Diisopropyl Adipate | | | | | 1 | | | 5 | | | |

TABLE 5-continued

Skin whitening compositions

| Ingredients | INCI-Name | 4 | 5 | 6 | 7 | 8 | 9 | 10 | 11 | 12 | 13 | 14 |
|---|---|---|---|---|---|---|---|---|---|---|---|---|
| Isodragol ® | Triisononanoin | | 2 | | | | | | | | | |
| Isopropyl Palmitate | Isopropyl Palmitate | | | | | | | | | | 13 | |
| Jaguar C-162 | Hydroxypropyl Guar, Hydroxypropyltrimonium Chloride | | | | | | | | | 0.1 | | |
| Jojoba Oil | Simmondsia Chinensis (Jojoba) Seed Oil | 1 | | | | | 2 | | | | | |
| Keltrol CG RD | Xanthan Gum | | 0.4 | 0.2 | 0.2 | 0.1 | | 0.05 | | | | |
| Lanette 16 | Cetyl Alcohol | | 1 | | | | | | | | | |
| Lanette O | Cetearyl Alcohol | | 0.5 | | | 3 | | | | | 5 | |
| Lara Care A-200 | Galactoarabinan | | 0.3 | | | | | | | | | |
| Luviskol K30 Powder | PVP | | | | | | | | | | | 3 |
| Magnesium Sulfate | Magnesium Sulfate | | | | | | 0.7 | | | | | |
| Mineral Oil | Mineral Oil | | | | | 8 | | ad 100 | | | | |
| Neo Heliopan ® 303 | Octocrylene | | 10 | 4 | | | | | | | 10 | |
| Neo Heliopan ® 357 | Butylmethoxydibenzoylmethane | | 3 | 2 | 3 | | | | | | 5 | |
| Neo Heliopan ® AP | Disodium Phenyl Dibenzimidazole Tetrasulfonate | 3 | | | | | | | | | | |
| Neo Heliopan ® AP, 15% sol., neutralized with Biotive ® L-Arginine | Aqua, Disodium Phenyl Dibenzimidazole Tetrasulfonate, Arginin | | | 6.7 | 6.7 | | | | | | | |
| Neo Heliopan ® E 1000 | Isoamyl p. Methoxycinnamate | | | 1 | | | | | | | | |
| Neo Heliopan ® HMS | Homosalate | | | 5 | | 5 | | | | | | |
| Neo Heliopan ® Hydro, 20% sol., neutralized with Biotive ® L-Arginine | Aqua, Phenylbenzimidazole Sulphonic Acid, Arginin | | | 10 | 10 | 10 | | | | | | |
| Neo Heliopan ® MBC | 4-Methylbenzylidene Camphor | | 1 | | | | | | | | | |
| Neo Heliopan ® OS | Ethylhexyl Salicylate | | | | 3 | 5 | | | | | | |
| Neutral Oil | Caprylic/Capric Triglyceride | | | | | | 6 | | | | 13.7 | |
| Ozokerite Wax 2389 | Ozokerite | | | | | | | | 2 | | | |
| PCL-liquid 100 | Cetearyl Ethylhexanoate | | | 2 | | 4 | 5 | | | | | |
| PCL-Solid | Stearyl Heptanoate, Stearyl Caprylate | | | | | 3 | | | 0.5 | | | |
| Phytoconcentrole ® Coconut | Caprylic/Capric Triglyceride, Coconut (Cococ Nucifera) Oil | | | | | | | | | 1 | | |
| Rewoderm LI S80 | PEG-200 Hydrogenated Palmitate, PEG-7 Glyceryl Cocoate | | | | | | | | | 0.25 | | |
| Rewopol SBFA30 | Disodium Laureth Sulfosuccinate | | | | | | | | | 8 | | |
| Silcare Silicone 41M65 | Stearyl Dimethicone | | | 1 | | | | | 21 | | | |
| Sodium Chloride | Sodium Chloride | | | | | | | | | 1.7 | | |
| Sodium Hydroxide 10% sol. | Sodium Hydroxide | | | | | | 0.9 | | | | | |
| Solubilizer | PEG-40 Hydrogenated Castor Oil, Trideceth-9, Propylene Glycol, Water (Aqua) | | | | | | | | 1.5 | | | 0.5 |

TABLE 5-continued

Skin whitening compositions

| Ingredients | INCI-Name | 4 | 5 | 6 | 7 | 8 | 9 | 10 | 11 | 12 | 13 | 14 |
|---|---|---|---|---|---|---|---|---|---|---|---|---|
| Sym3D ® | Hydroxymethoxy phenyl Propylmethylmethoxybenzofuran | | | 0.2 | | | | | | | | |
| SymCalmin ® | Pentylene Glycol, Butylene Glycol, Hydroxyphenyl Propamidobenzoic Acid | | | | | 1 | | | | | | |
| SymClariol ® | Decylene Glycol | | | 0.5 | | | | | | | | |
| SymDiol ® 68 | 1,2 Hexanediol, Caprylyl Glycol | 0.6 | | | | | | 1 | | | | |
| SymFinity ® 1298 | *Echinacea Purpurea* Extract | | | 0.5 | | | | | | | | |
| SymFit ® 1617 | Trimethylcyclohexyl Butylcarbamate | | | | | | 0.1 | | | | | |
| SymFit ® nat 1750 | Propanediol, *Bobgunnia Madagascariensis* Wood Extract | | | | 1 | | | | | | | |
| SymGlucan ® | Water (Aqua) Glycerin, Beta Glucan | | 2 | | 2 | 1 | | 5 | | | | |
| SymHelios ®1031 | Benzylidene Dimethoxydimethylindanone | | | 0.5 | 0.5 | | | | | | | |
| SymMatrix ® | Maltodextrin, *Rubus Fruticosus* (Blackberry) Leaf Extract | | | | | 0.5 | | | | | | |
| SymMollient ® L | Neopentyl Glycol Diisononanoate | | | | 2 | | | | | | 5 | |
| SymMollient ® S | Cetearyl Nonanoate | | | | 1 | | | | | | 4 | |
| SymMollient ® W/S | Trideceth-9, PEG-5 Isononanoate | | | | | | | 2 | | | | |
| SymOcide ® PS | Phenoxyethanol, Decylene Glycol, 1,2-Hexanediol | | | | | | 0.7 | | | | | |
| SymRelief ® 100 | Bisabolol, *Zingiber Officinale* (Ginger) Root Extract | | | | | | | | 0.1 | | | |
| SymRelief ® S | Bisabolol, Hydroxymethoxy phenyl Decanone | | | 0.1 | | 0.2 | | | | | | |
| SymRepair ® | Hexyldecanol, Bisabolol, Cetylhydroxyproline Palmitamide, Stearic Acid, *Brassica Campestris* | | | | 1 | | 3 | | | | | |
| SymSitive ®1609 | Pentylene Glycol, 4-t-Butylcyclohexanol | | | | | 0.5 | | | | | | |
| SymVital ® | *Aloe Barbadensis* Leaf Juice Powder, Magnesium Ascorbyl Phosphate, *Rubus Idaeus* | 0.5 | | | | | | 0.1 | | | | |
| Tinosorb S | Bis-Ethylhexyloxyphenol, Methoxyphenyl Triazine | | | | | | | | | | 3 | |
| Tapioca Pure | Tapioca Starch | | 5 | | | | | | | | | |
| TeCe-Ozokerit N502 | Ozokerite | | | | | | | | | | ad 100 | |
| Tego Betain L7 | Cocoamidopropyl Betaine | | | | | | | | | 5 | | |
| Tegosoft TN | C12-15 Alkyl Benzoate | | | | 5 | | | | | | | |
| Texapon N70 | Sodium Laureth Sulfate | | | | | | | | | 15 | | |

TABLE 5-continued

| | | Skin whitening compositions | | | | | | | | | |
|---|---|---|---|---|---|---|---|---|---|---|---|
| Ingredients | INCI-Name | 4 | 5 | 6 | 7 | 8 | 9 | 10 | 11 | 12 | 13 | 14 |
| Triethanolamine 99% | Triethanolamine | | | | | | | | | | | 0.5 |
| Vitamin E acetat | Tocopherol Acetate | | 0.5 | 0.5 | 0.5 | | 0.2 | | 0.5 | | 0.7 | |
| Wacker-Belsil CDM3526 VP | C26-C28 Alkyl Dimethicone | | | | | | | | | | 2 | |
| Water, demin. | Water (Aqua) | ad 100 | ad 100 | ad 100 | ad 100 | ad 100 | ad 100 | ad 100 | | ad 100 | | ad 100 |

Examples 15 to 22

Deodorant and Antiperspirant Formulations

Example 15

Deodorant Roll-on (Amounts in % b.w.)

| Ingredients | INCI | 15 |
|---|---|---|
| Butylene Glycol | Butylene Glycol | 2.00 |
| SymSol PF 3 | Water (Aqua), Pentylene Glycol, Sodium Lauryl Sulfoacetate, Sodium Oleoyl Sarcosinate, Sodium Chloride, Disodium Sulfoacetate, Sodium Oleate | 2.00 |
| SymDeo ® B125 | 2-Methyl 5-Cyclohexylpentanol | 0.50 |
| Hydroviton ® Plus | Water (Aqua), Pentylene Glycol, Glycerin, Fructose, Urea, Citric Acid, Sodium Hydroxide, Maltose, Sodium PCA, Sodium Chloride, Sodium Lactate, Trehalose, | 2.0 |
| Dragosantol 100 | Bisabolol | 0.10 |
| Larixol | | 0.30 |
| Natrosol Hydroxyethylcellulose | Hydroxyethylcellulose | 0.50 |
| Phenoxyethanol | Phenoxyethanol | 0.30 |
| Fragrance | Fragrance | 0.30 |
| Water | Water (Aqua) | Ad 100 |

Example 16

Clear Deodorant Antiperspirant Roll-on (Amounts in % b.w.)

| Ingredients | INCI | 16 |
|---|---|---|
| Methocel E4M Premium | Hydroxypropyl Methylcellulose | 0.50 |
| Water | Water (Aqua) | Ad 100 |
| SymMollient ® W/S | Trideceth-9, PEG-5 Isononanoate, Water (Aqua | 1.00 |
| Solubilizer | PEG-40 Hydrogenated Castor Oil, Trideceth-9, Propylene Glycol, Water (Aqua) | 3.00 |
| Deolite | Dimethyl Phenylpropanol, Pentylene Glycol | 0.50 |
| Locron L | Aluminium Chlorohydrate | 25.00 |
| Aloe Vera Gel Concentrate | Aloe Barbadensis Leaf Juice | 1.00 |
| Propylene Glycol -1,2 | Propylene Glycol | 4.00 |
| Larixol | | 0.05 |
| Ethanol 96% | Alcohol Denat. | 30.00 |
| Fragrance | Fragrance | 1.00 |

Example 17

Deodorant Stick (Amounts in % b.w.)

| Ingredients | INCI | 17 |
|---|---|---|
| Sodium Stearate | Sodium Stearate | 8.00 |
| SymRepair ® 100 | Hexyldecanol, Bisabolol, Cetylhydroxyproline Palmitamide, Stearic Acid, Brassica Campestris (Rape-seed) Sterols | 1.00 |
| Tegosoft APM | PPG-3 Myristyl Ether | 70.00 |
| 1,2-propylene Glycol | Propylene Glycol | 10.00 |
| SymClariol ® | Decylene Glycol | 1.00 |
| SymDeo ® MPP | Dimethyl Phenylbutanol | 0.50 |
| Larixol | | 0.05 |
| Fragrance | Fragrance | 1.0 |
| Water | Water (Aqua) | Ad 100 |

Example 18

Zirconium Suspensoid Antiperspirant Stick (Amounts in % b.w.)

| Ingredients | INCI | 18 |
|---|---|---|
| PCL Liquid 100 | Cetearyl Ethylhexanonate | Ad 100 |
| Silicone Fluid 345 | Cyclomethicone | 10.00 |
| Crodacol C90 | Cetyl Alcohol | 8.00 |
| Symcrowax HGLC | C18-36 Triglyceride | 8.00 |
| SymClariol ® | Decylene Glycol | 1.00 |
| Larixol | | 0.30 |
| Crodamol PTC | Pentaerythritol Tetracaprylate/Caprate | 5.00 |
| Syncrowax HRC | Tribehenin | 4.00 |
| Volpo N5 | Oleth-5 | 1.00 |
| Titanium Dioxide | Titanium Dioxide | 1.00 |
| Rezal 36GP | Aluminium Tetrachlorohydrex GLY | 20.00 |
| Dry Flo C | Aluminium Starch Octenyl Succinate | 22.50 |
| Preservative | Phenoxyethanol | 0.8 |
| Fragrance | Fragrance | 1.0 |

Examples 19 to 20

Deodorant Pump Spray with and without 30% Ethanol

| Ingredients | INCI | 19 | 20 |
|---|---|---|---|
| SymClariol ® | Decylene Glycol | 0.50 | 0.50 |
| Solubilizer | PEG-40 Hydrogenated Castor Oil, Trideceth-9, Propylene Glycol, Water | 4.00 | 2.00 |

-continued

| Ingredients | INCI | 19 | 20 |
|---|---|---|---|
| Neo-PCL Water Soluble N | Trideceth-9, PEG-5 Ethylhexanoate, Water (Aqua) | 1.50 | 1.50 |
| Larixol | | 0.3 | 0.05 |
| SymSitive ® 1609 | Pentylene Glycol 4-t-Butylcyclohexanol | 1.0 | 1.0 |
| SymRelief ® 100 | Bisabolol, *Zingiber Officinale* | 0.10 | 0.10 |
| Water | Water (Aqua) | Ad 100 | Ad 100 |
| 1,2 Propylene Glycol | Propylene Glycol | 6.00 | 6.00 |
| SymDiol ® 68 | 1,2-Hexanediol, Caprylyl Glycol | 0.80 | 0.80 |
| Ethanol | Ethanol | — | 30.00 |
| Fragrance | Fragrance | 0.5 | 0.5 |

Example 21

Deodorant Roll-on Emulsion (Amounts in % b.w.)

| Ingredients | INCI | 21 |
|---|---|---|
| Dracorin ®GOC | Glyceryl Oleate Citrate, Caprylic/Capric Triglyceride | 2.0 |
| SymMollient ®S | Cetearyl Nonanoate | 0.5 |
| Isodragol ® | Triisononanoin | 2.0 |
| Neutral Oil | Caprylic/Capric Triglyceride | 3.5 |
| SymCalmin ® | Pentylene Glycol, Butylene Glycol, Hydroxyphenyl Propamidobenzoic Acid | 1.0 |
| Xiameter PMX-0246 | Cyclohexasiloxane | 1.0 |
| Deolite | Dimethyl Phenylpropanol, Pentylene Glycol | 0.5 |
| Frescolat ® X-Cool | Menthyl Ethylamido Oxalate | 1.0 |
| Fragrance | Fragrance | 0.6 |
| Pemulen TR1 | Acrylates/10-30 Alkyl Acrylate Crosspolymer | 0.25 |
| Water | Water (Aqua) | Ad 100 |
| Glycerin | Glycerin | 2.0 |
| SymDiol ® 68 T | 1,2 Hexanediol, Caprylyl Glycol, Tropolone | 0.7 |
| Larixol | | 0.2 |
| SymWhite 377 | Phenylethyl resorcinol | 0.3 |
| NaOH 10% sol. | Sodium Hydroxide | 0.6 |

Example 22

Deodorant Spray, Aerosol (Amounts % b.w.)

| Ingredients | INCI | 22 |
|---|---|---|
| Ethanol, 96% | Ethanol | 26.5 |
| Larixol | | 0.2 |
| SymDeo ® MPP | Dimethyl Phenylbutanol | 0.50 |
| Dragoxat 89 | Ethylhexyl Isononanoate | 1.0 |
| PCL Liquid 100 | Cetearyl Ethylhexanoate | 1.0 |
| Fragrance | Fragrance | 1.0 |
| Propane/Butane | Propane Butane (2.7 bar) | ad 100 |

Examples 23-33

Oral Care Products

Example 23

Gel Dental Cream (Amounts % b.w.)

| Ingredients | 23 |
|---|---|
| Na carboxymethylcellulose | 0.40 |
| Sorbitol 70%, in water | 72.00 |
| Polyethylene glycol (PEG) 1500 | 3.00 |
| Na saccharinate | 0.07 |
| Na fluoride | 0.24 |
| p-Hydroxybenzoic acid (PHB) ethyl ester | 0.15 |
| Peppermint aroma | 1.00 |
| Larixol | 1.00 |
| Abrasive silica | 11.00 |
| Thickening silica | 6.00 |
| Sodium dodecyl sulfate (SDS) | 1.40 |
| Dist. water | to 100.00 |

Example 24

Dental Cream Against Plaque (Amounts % b.w.)

| Ingredients | 24 |
|---|---|
| Carrageenan | 0.90 |
| Glycerin | 15.00 |
| Sorbitol 70%, in water | 25.00 |
| PEG 1000 | 3.00 |
| Tetrapotassium diphosphate | 4.50 |
| Tetrasodium diphosphate | 1.50 |
| Na saccharinate + Na fluoride | 0.64 |
| Precipitated silica | 20.00 |
| Titanium dioxide | 1.00 |
| Spearmint aroma | 1.10 |
| Larixol | 0.80 |
| Sodium dodecyl sulfate | 1.30 |
| Dist. water | to 100.00 |

Example 25

Dental Cream Against Sensitive Teeth (Amounts % b.w.)

| Ingredients | 25 |
|---|---|
| Na carboxymethylcellulose | 0.70 |
| Xanthan gum | 0.50 |
| Glycerin | 15.00 |
| Sorbitol 70%, in water | 12.00 |
| K nitrate | 5.00 |
| Na monofluorophosphate | 0.80 |
| PHB methyl ester | 0.15 |
| PHB propyl ester | 0.05 |
| Na saccharinate | 0.20 |
| *Eucalyptus*/menthol aroma | 1.00 |
| Larixol | 0.20 |
| Ca carbonate | 35.00 |
| Silicon dioxide | 1.00 |
| Sodium dodecyl sulfate (SDS) | 1.50 |
| Dist. water | to 100.00 |

Example 26

Ready-to-Use Mouthwash with Fluoride (Amounts % b.w.)

| Ingredients | 26 |
|---|---|
| Ethanol | 7.00 |
| Glycerin | 12.00 |
| Na fluoride | 0.05 |
| Pluronic F-127 ® (BASF, surface-active substance) | 1.40 |
| Na phosphate buffer pH 7.0 | 1.10 |
| Sorbic acid | 0.20 |
| Na saccharinate | 0.10 |
| Cinnamon/menthol aroma | 0.15 |
| Larixol | 0.40 |
| Dyestuff | 0.01 |
| Dist. water | to 100.00 |

Example 27

Mouthwash Concentrate (Amounts % b.w.)

| Ingredients | 27 |
|---|---|
| Ethanol, 95% strength | 80.00 |
| Na cyclamate | 0.15 |
| *Eucalyptus*/wintergreen aroma | 3.50 |
| Dyestuff | 0.01 |
| Larixol | 1.20 |
| Dist. water | to 100.00 |

Example 28

Chewing Gum (Amounts % b.w.)

| Ingredients | 28 |
|---|---|
| Chewing gum base | 21.00 |
| Glucose syrup | 16.50 |
| Glycerin | 0.50 |
| Powdered sugar | 59.3 |
| Spearmint aroma | 1.50 |
| Larixol | 0.30 |

Example 29

Sugar-Free Chewing Gum (Amounts % b.w.)

| Ingredients | 29 |
|---|---|
| Chewing gum base | 30.00 |
| Sorbitol, powder | ad 100 |
| Palatinite | 9.50 |
| Xylitol | 2.00 |
| Mannitol | 3.00 |
| Aspartame | 0.20 |
| Emulgum/emulsifier | 0.30 |
| Sorbitol 70%, in water | 14.00 |
| Glycerin | 1.00 |
| Cinnamon/menthol aroma | 1.50 |
| Larixol | 0.80 |

Example 30

Gelatine Capsules for Direct Consumption (Amounts % b.w.)

| Ingredients | 31 |
|---|---|
| Gelatine shell: | |
| Glycerin | 2.014 |
| Gelatine 240 Bloom | 7.91 |
| Sucralose | 0.065 |
| Allura Red | 0.006 |
| Brilliant Blue | 0.005 |
| Core composition: | |
| Plant oil triglyceride | 82.00 |
| Aroma B# | 7.85 |
| Larixol | 0.50 |

Aroma B here had the following composition (data in each case in wt. %): 0.1% neotame powder, 0.05% aspartame, 29.3% peppermint oil arvensis, 29.3% peppermint piperita oil Willamette, 2.97% sucralose, 2.28% triacetin, 5.4% diethyl tartrate, 12.1% peppermint oil yakima, 0.7% ethanol, 3.36% 2-hydroxyethyl menthyl carbonate, 3.0% 2-hydroxypropyl menthyl carbonate, 0.27% vanillin, 5.5% D-limonene, 5.67% L-menthyl acetate.

The gelatine capsule, which is suitable for direct consumption, had a diameter of 5 mm, and the weight ratio of core material to shell material was 90:10. The capsules opened in the mouth within less than 10 seconds and dissolved completely within less than 50 seconds.

Example 31

Fruit Gums (Amounts in % .w.)

| Ingredients | 31 |
|---|---|
| Water | to 100 |
| Saccharose | 34.50 |
| Glucose syrup, DE 40 | 31.89 |
| Iso Syrup C* Tru Sweet 01750 (Cerestar GmbH) | 1.50 |
| Gelatine 240 Bloom | 8.20 |
| Yellow and red colouring | 0.01 |
| Citric acid | 0.20 |
| Larixol | 0.10 |

Example 32-33

Hard Caramel (Hard Boiled Candy) (Amounts in % b.w.)

| Ingredients | 32 | 33 |
|---|---|---|
| Sugar (sucrose) | to 100 | to 100 |
| Maize syrup (corn syrup), contains glucose and fructose | 41.00 | 41.00 |
| Maltose | 3.00 | 3.00 |
| Palm kernel oil | 0.90 | 0.90 |
| Citric acid | 0.30 | 0.30 |
| *Ginseng* extract | — | 0.40 |
| Blue dyestuff | 0.01 | 0.01 |
| Larixol | 0.50 | 0.10 |
| Honey | — | 1.50 |
| Honey flavour | — | 0.30 |

The sugar, corn syrup and maltose were dissolved in water and the solution was boiled and placed under a vacuum. The remaining ingredients were then sucked into the boiled sugar mass and the mixture was homogenized at the boiling temperature. After cooling, hard caramels were stamped out of the resulting mass. The hard caramels showed residual water content of about 2.5%.

What claimed is:

1. A composition comprising the combination of larixol and phenylethyl resorcinol in a ratio by weight of about 20:80 to about 80:20, respectively.

2. The composition of claim 1, further comprising primary sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivatives and indole derivatives, and mixtures thereof.

3. The composition of claim 1, further comprising secondary sun protection factors selected from the group consisting of amino acids and derivatives thereof imidazoles and derivatives thereof, D,L-carnosine, D-carnosine, L-carnosine and derivatives thereof, carotenoids, carotenes and derivatives thereof chlorogenic acid and derivatives thereof, liponic acid and derivatives thereof aurothioglueose, propylthiouracil and other thiols, dilaurylthiodipropionate, distearylthiodipropionate, thiodipropionic acid and derivatives thereof sulfoximine compounds, humic acid, bile acid, bile extracts, bilirubin, biliverdin, B.DTA, EGTA and derivatives thereof unsaturated fatty acids and derivatives thereof folic acid and derivatives thereof ubiquinone and ubiquinol and derivatives thereof vitamin C and derivatives thereof, tocopherols and derivatives, coniferyl benzoate of benzoin resin, rutinic acid and derivatives thereof glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof mannose and derivatives thereof superoxide dismutase, titanium dioxide, zinc and derivatives thereof selenium and derivatives thereof, stilbenes and derivatives thereof and mixtures thereof.

4. The composition of claim 1, further comprising antioxidants selected from the group consisting of vitamin A and derivatives, vitamin C and derivatives, tocopherol and derivatives and mixtures thereof.

5. The composition of claim 1, further comprising anti-inflammatory agents (component b4) are selected from the group consisting of corticosteroids, salicylates acetic acid derivatives, fenamates, propionic acid derivatives, pyrazoles, anthranilic acid derivatives, alpha-bisabolol, apigenin, apigenin-7-gincoside, gingerols, shogaols, gingerdiols, dehydrogingerdiones, paradols, tranilast, avenanthramide A, avenanthramide B, avenanthramide C, boswellic acid, phytosterols, glycyrrhizin, and licochalcone A, allantoin, panthenol, lanolin, (pseudo-) ceramides, glycosphingolipids, phytosterols, chitosan, mannose, lactose, β-glucans, and extracts or fractions from camomile, aloe vera, oats, calendula, *arnica*, honeysuckle, rosemary, witch hazel, ginger or *echinacea*, and mixtures thereof.

6. The composition of claim 1, further comprising desquamating agents selected from the group consisting of sulphonic acids, calcium chelators, ascorbic acid and its derivatives, nicotinamide, urea, (N-2-hydroxyethylpiperazine-N-2-ethane)sulphonic acid (HEPES), β-hydroxy acids, retinoids and mixtures thereof.

7. The composition of claim 1, wherein larixol is present in an amount of about 000001 to about 30% b.w.—calculated on the final composition.

8. The composition of claim 1, wherein the phenylethyl resorcinol is present in an amount of about 0.00001 to about 30% b.w.—calculated on the final composition.

9. The composition of claim 1, further comprising additional ingredients sun protection factors; antioxidants; anti-inflammatory agents; and desquamation agents, independently from each other are present in an amount of about 0.00001 to about 30% b.w.—calculated on the final composition.

10. The composition of claim 1, wherein said composition is selected from the group consisting of a cosmetic composition, a pharmaceutical composition and a dietary supplement composition.

11. A medicament for inhibiting melanin formation in melanocytes or interleukin- (IL-) 1α biosynthesis containing the composition of claim 1.

12. A non-therapeutical method for lightening skin and hair by applying a working amount of the composition of claim 1 to a human.

13. A preparation comprising the composition of claim 1 wherein the preparation is selected from the group consisting of a foot care, product, an insect repellent, a shaving product, aftershave balm, pre-shave lotion, a dietary supplement, a candy, and a chewing gum.

14. A hair-lightening preparation comprising the composition of claim 1.

15. The composition of claim 1 further comprising at least one of the components (b1) to (b5) selected from:
   (b1) tyrosinase inhibitors selected from the group consisting of kojic acid, beta- and alpha-arbutin, hydroquinone, nicotinamide, dioic acid, Mg ascorbyl phosphate and vitamin C and its derivatives, mulberry extract, Bengkoang extract, *papaya* extract, turmeric extract, nutgrass extract, licorice extract containing glycyrrhizin, alpha-hydroxy-acids, 4-alkylresorcinols, 4-hydroxyanisole and mixtures thereof;
   (b2) sun protection factors;
   (b3) antioxidants
   (b4) antiinflammatory agents; and
   (b5) desquamating agents.

* * * * *